(12) United States Patent  
Zhang et al.

(10) Patent No.: US 7,810,374 B2  
(45) Date of Patent: Oct. 12, 2010

(54) SINGLE SOLDER BALL IMPACT TESTER

(75) Inventors: Zheming Zhang, Hong Kong (CN); Jingshen Wu, Hong Kong (CN)

(73) Assignee: The Hong Kong University of Science and Technology, Kowloon (HK)

( * ) Notice: Subject to any disclaimer, the term of this patent is extended or adjusted under 35 U.S.C. 154(b) by 73 days.

(21) Appl. No.: 12/314,021

(22) Filed: Dec. 2, 2008

(65) Prior Publication Data

US 2009/0139303 A1     Jun. 4, 2009

Related U.S. Application Data

(60) Provisional application No. 60/996,718, filed on Dec. 3, 2007.

(51) Int. Cl.  
*G01M 7/00* (2006.01)

(52) U.S. Cl. .......................... 73/12.09; 73/841

(58) Field of Classification Search ..... 73/12.01–12.14, 73/841

See application file for complete search history.

(56) References Cited

U.S. PATENT DOCUMENTS

| | | | |
|---|---|---|---|
| 6,078,387 A | 6/2000 | Sykes | |
| 6,260,998 B1 * | 7/2001 | Garfinkel et al. | ............... 374/57 |
| 6,301,971 B1 | 10/2001 | Sykes | |
| 6,341,530 B1 | 1/2002 | Sykes | |
| 6,871,525 B2 * | 3/2005 | Withnall et al. | ............ 73/12.14 |
| 7,329,900 B2 | 2/2008 | Yeh et al. | |
| 7,412,870 B2 | 8/2008 | Brankov | |
| 7,500,378 B2 * | 3/2009 | Tsai et al. | .................. 73/12.09 |
| 2006/0292711 A1 * | 12/2006 | Su et al. | ....................... 438/14 |

FOREIGN PATENT DOCUMENTS

WO    WO 2008/003948 A1    1/2008

OTHER PUBLICATIONS

Zhang, F., et al., "Failure Mechanism of Lead-Free Solder Joints in Flip Chip Packages", *Journal of Electronic Materials*, vol. 31, No. 11, pp. 1256-1263, (Nov. 2002).

(Continued)

*Primary Examiner*—Max Noori  
(74) *Attorney, Agent, or Firm*—The Nath Law Group; Jerald L. Meyer; Stanley N. Protigal

(57) ABSTRACT

A test apparatus applies high speed impact load to a sample to test the shear strength of attachment of a component part to the sample, by use of a rotary drive mechanism driving an impact tip. A support mechanism provides alignment between the impact tip and a portion of the sample to receive a test force, and prevents relative movement of at least one of the sample and the impact tip. The rotary drive mechanism establishes a impact force between the impact tip and the sample, and a force transducer receives the resultant force and providing a corresponding output. In one example the force transducer uses a piezoelectric film for sensing. The testing may be used, for example, to provide stable impact speed to a solder ball, and provide, as an output a force and displacement relationship curve. The stable speed can be acquired by clutch, and the data collection.

21 Claims, 8 Drawing Sheets

OTHER PUBLICATIONS

Chang-Bae Lee, et al., "Intermetallic compound layer formation between Sn-3.5 mass % Ag BGA solder ball and (Cu, immersion Au / electroless Ni-P / Cu) substrate", *Journal of materials Science: Materials in Electronics*, vol. 14, pp. 487-493, (2003).

JESD22-B111, JEDEC "Board Level Drop Test Method of Components for Handheld Electronic Products", *JEDEC Solid State Technology Association*, Electronic Industries Alliance, (Jul. 2003).

JESD22-B117A, JEDEC, "Solder Ball Shear", *JEDEC Solid State Technology Association*, Electronic Industries Alliance, (Oct. 2006).

JESD22-B110A, JEDEC "Subassembly Mechanical Shock", *JEDEC Solid State Technology Association*, Electronic Industries Alliance, (Nov. 2004).

Newman, K., et al., "BGA Brittle Fracture-Alternative Solder Joint Integrity Test Methods", *2005 Electronic Components and Technology Conference*, pp. 1194-1201, (2005).

Date, M., et al., "Impact Reliability of Solder Joints", *2004 Electronics Components and Technology Conference*, pp. 668-674, (2004).

Chang-Lin Yeh et al., "Design Guideline for Ball Impact Test Apparatus", *Journal of Electronic Packing*, Transactions of the ASME, vol. 129, pp. 98-104, (Mar. 2007).

XYZTEC, Impact Measurement Unit Specifications XYZTEC IMU, pp. 1-2, (Jun. 2008).

XYZTEC, Pendulum Specifications for XYZTEC IMU, p. 1, (Jun. 2008).

XYZTEC, Pendulum Micro Impact Tester Power Point, Impact Measurement Unit IMU, XYZTEC 2008, pp. S1-S38.

* cited by examiner

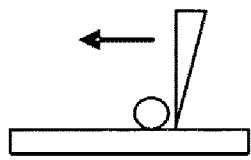
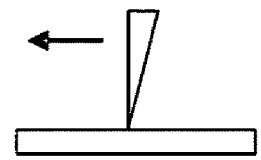
Fig. 1A
*(prior art)*
Fig. 1B
*(prior art)*
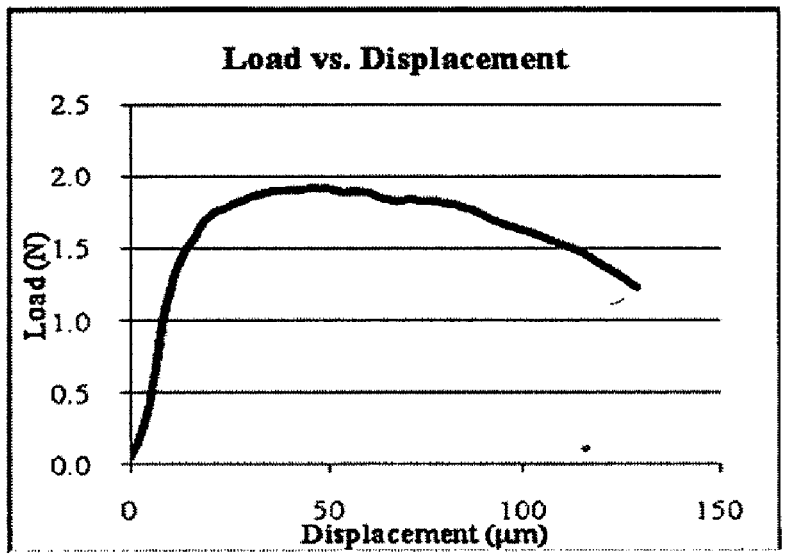
Fig. 2
*(prior art)*
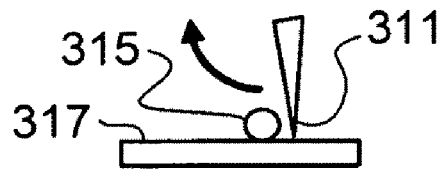
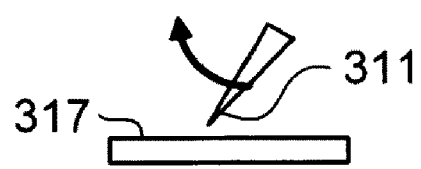
Fig. 3A
Fig. 3B

SINGLE SOLDER BALL IMPACT TESTER

RELATED APPLICATION

The present patent application claims priority to Provisional Patent Application No. 60/996,718 filed Dec. 3, 2007, which is filed by the inventors hereof and which incorporated by reference herein.

BACKGROUND

1. Field

This disclosure relates to measuring and testing, and more particularly to testing of solder balls and similar structures, such as found in a ball grid array.

2. Background

Because ball grid arrays (BGAs) have a wide application in electronic packaging, the packaging strength of BGAs to the attachment substrate is crucial for industry. Industry uses a test procedure called a "single ball shear test", which provides a simple and efficient technique for evaluating the quality of solder balls. Experimental observations from low shear rate tests of solder joints are not accurate predictors of failure behaviour at high strain rates. That is because low shear rate tests of solder joints cannot accurately predict the mode of deformation and failure behavior at high strain rates. Due to strain rate effect, brittle failures often take place when the solder joints are subjected to dynamic loadings, and such brittle failures may not be seen under low strain rate shear tests.

Thus, it is desired to develop an improved test procedure capable of evaluating the impact strength characterization of component parts. One such example is a procedure for evaluating the impact strength characterization of solder joints. Such impact strength characterization becomes critical during package design and manufacturing for high reliability. This is particularly true for lead-free solder, for example, lead-free solder used in handheld devices.

Conventional techniques of testing solder balls use a linear accelerating system to shear the solder ball at different speeds. FIGS. 1A and 1B are schematic diagrams showing the movement of a tester tip against a solder ball. As FIGS. 1A and 1B depict, the tip moves in the linear direction from a significant distance. At an expected speed, the tip will shear the solder ball, resulting in the removal of the solder ball (FIG. 1B). FIG. 2 is a graph showing measured load vs. displacement. During this impact situation, the force versus displacement curve will be recorded, resulting in a graph as shown in FIG. 2. The load may be measured at the tip's holder or at the clamp for the substrate to which the solder ball is attached. From the curve depicted in FIG. 2, the resistance of shearing the solder ball can be observed.

SUMMARY

A test is performed by an apparatus applying a high speed impact load to a sample to test the shear strength of attachment of a component part to the sample. A support mechanism provides an alignment between an impact tip and a portion of the sample to receive a test force, and prevents relative movement of at least one of the sample and the impact tip. A rotary drive mechanism applies relative motion between the tip and the sample to establishing an impact force between the impact tip and the sample, and a force transducer receives a force proportional to said impact force and provides a corresponding output.

BRIEF DESCRIPTION OF THE DRAWING

FIGS. 1A and 1B are schematic diagrams showing the movement of a tester tip against a solder ball.

FIG. 2 is a graph showing measured load vs. displacement.

FIGS. 3A and 3B are schematic diagrams showing rotational movement of a tester tip against a solder ball, implementing a rotational accelerating system.

DETAILED DESCRIPTION

Overview

Good solder joint strength at high strain rates is a critical reliability requirement for portable electronic devices. Experimental observation from low shear rate tests of solder ball joints cannot precisely reflect their deformation and failure behaviors at high strain rates.

Testing of solder balls is given by way of non-limiting example. The testing apparatus is designed to test the strength of single solder ball in one chip. It can provide stable impact speed to a single solder ball, and at the same time to acquire its force and displacement relationship curve. The stable speed can be acquired by clutch, and the data collection can be obtained by piezoelectric film. The example solder ball testing demonstrates an ability to perform impact testing with short-range acceleration, controllable impact momentum and provides accurate measurement.

The technique provides impact testing for a wide variety of general product reliability testing involving impact or force measurements. The technique is performed with short-distance acceleration, controllable impact speed and provides accurate measurement.

Figure 4:
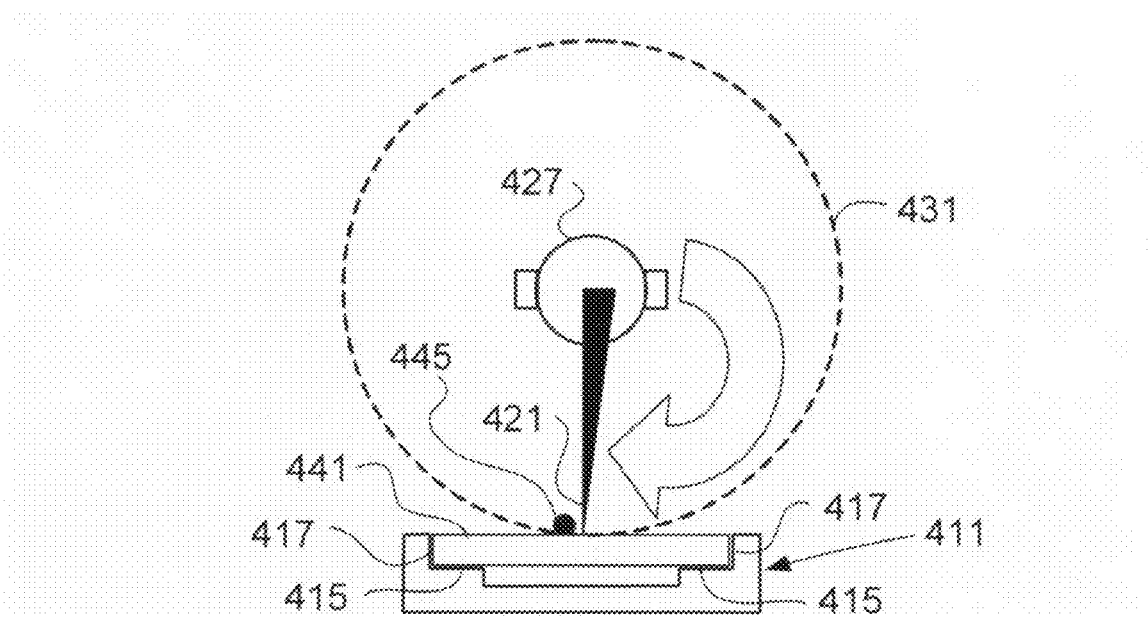
FIG. 4 is a diagram showing the basic components of the rotational accelerating system.
Figure 5:
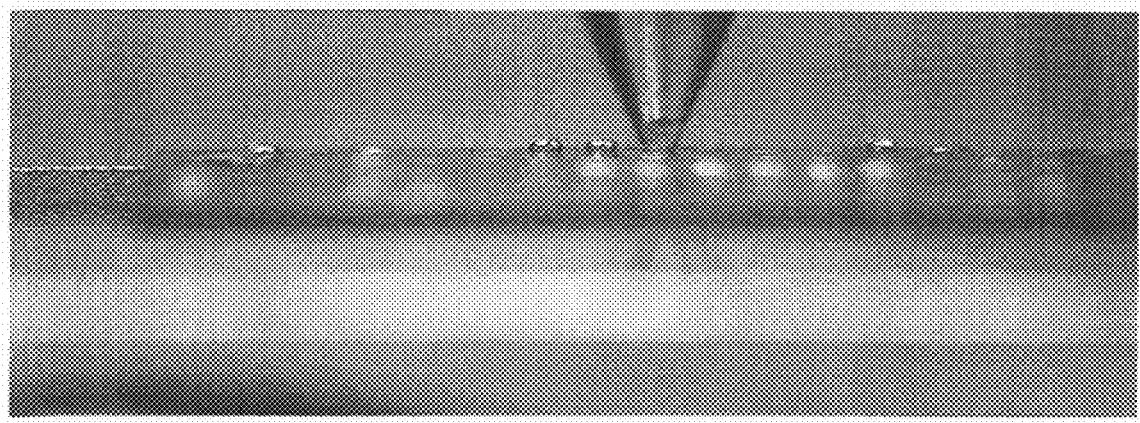
FIG. 5 is a photomicrograph showing the engagement of a tester tip with a solder ball on a substrate.

FIGS. 3A and 3B are schematic diagrams showing rotational movement of a tester tip 311 against a solder ball 315 fused to a substrate 317, implementing a rotational accelerating system. The rotational accelerating system is used to replace the former linear acceleration system to shear the solder ball. FIG. 4 is a diagram showing the basic components of the rotational accelerating system. FIG. 4 depicts a sampling platform 411 consisting of resting surface 415 and clamp 417. Tester tip 421 is controlled by motor 427 to rotate in an arc indicated at dashed circular line 431. A sample substrate 441 is placed on sampling platform 411 and clamped by clamp 417. Solder ball 445 on sample 441 is engaged by tip 421, and if the force exerted by tip 421 exceeds the fusion strength of solder ball 445 to substrate 441, solder ball is destructively removed. FIG. 5 is a photomicrograph showing the engagement of a tester tip with a solder ball on a substrate.

By using the rotational accelerating system, the speed can be more accurately controlled and the displacement for speed acceleration will be shorter than is the case with a conventional linear accelerating system. Less displacement for accelerating results in less solder balls being affected during the test, and more information concerning the solder balls will be obtained.

In order to acquire impact data, a new sensor-piezoelectric film is used. This sensor can produce an electrical output by pressure force, and it has a high sampling rate, which is necessary for high speed impact on one single solder ball. Compared with the former sensor design, this design has low vibration effect from mechanical waves caused by dynamic loading.

By using this testing method, more solder balls can be tested compared to linear accelerating system. This increase in number of solder balls tested is due, in part, to the accelerating distance being much shorter in the rotational accelerating system than in a linear accelerating system.

Configuration

Figure 6:
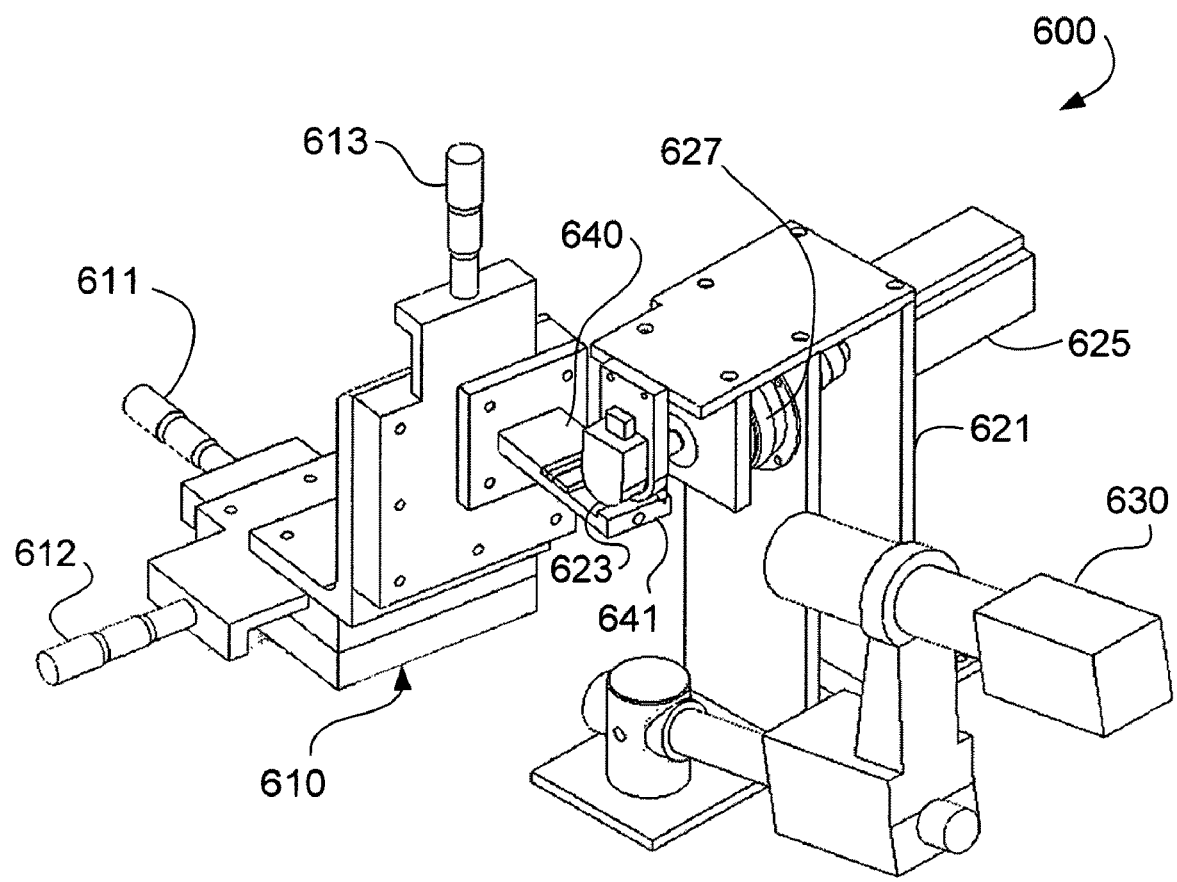
FIG. 6 is a diagram showing a configuration of a tester.

FIG. 6 is a diagram showing a configuration of a tester 600 used to perform the functions diagramed in FIG. 4. The major components of the tester of FIG. 6 include four parts:

alignment system 610, which includes adjusters 611, 612, 613;

impact system, which includes support 621, impact tip 623, motor 625 and clutch 627;

monitor system 630; and platform and sampling system 640, which includes clamp 641.

Clamp 641 is used to support a sample (not shown in FIG. 6; see sample substrate 441 with solder ball 445, FIG. 4). Clamp 641 is used to apply a pre-tightening load to the substrate (441, FIG. 4). The pre-tightening load allows measurement of force at clamp 641, as will be explained infra.

Adjusters 611, 612, 613 on alignment system 610 provides adjustment as an X-Y-Z table. The X-Y-Z adjustment preciously locates platform and sampling system 640, and is used to put the solder ball in alignment with impact tip 623.

Impact System

The impact follows five steps:

Step 1: The sample is aligned in three directions by XYZ table 610.

Step 2: The ram height is adjusted.

Step 3: After alignment, impact tip 623 is rotated in an arc away from the front of the single solder ball. This allows for acceleration of impact tip 623.

Step 4: Impact tip 623 is accelerated to a stable speed prior to engaging the solder ball.

Step 5: The solder ball is impacted by tip 623.

In order to complete the impact, it is desired to establish a desired rotational impact speed of tip 623. The acceleration system comprising motor 625 and clutch 627 is designed to provide stable impact speed. The use of a clutch allows the tip to acquire speed within a short time period and further allows the drive mechanism to provide a desired momentum without the motor being restricted to the arc of movement of the impact tip. In the example configuration, the impact speed is selected from a range of 0.3 m/s to 5 m/s.

Impact Drive System

Figure 7:
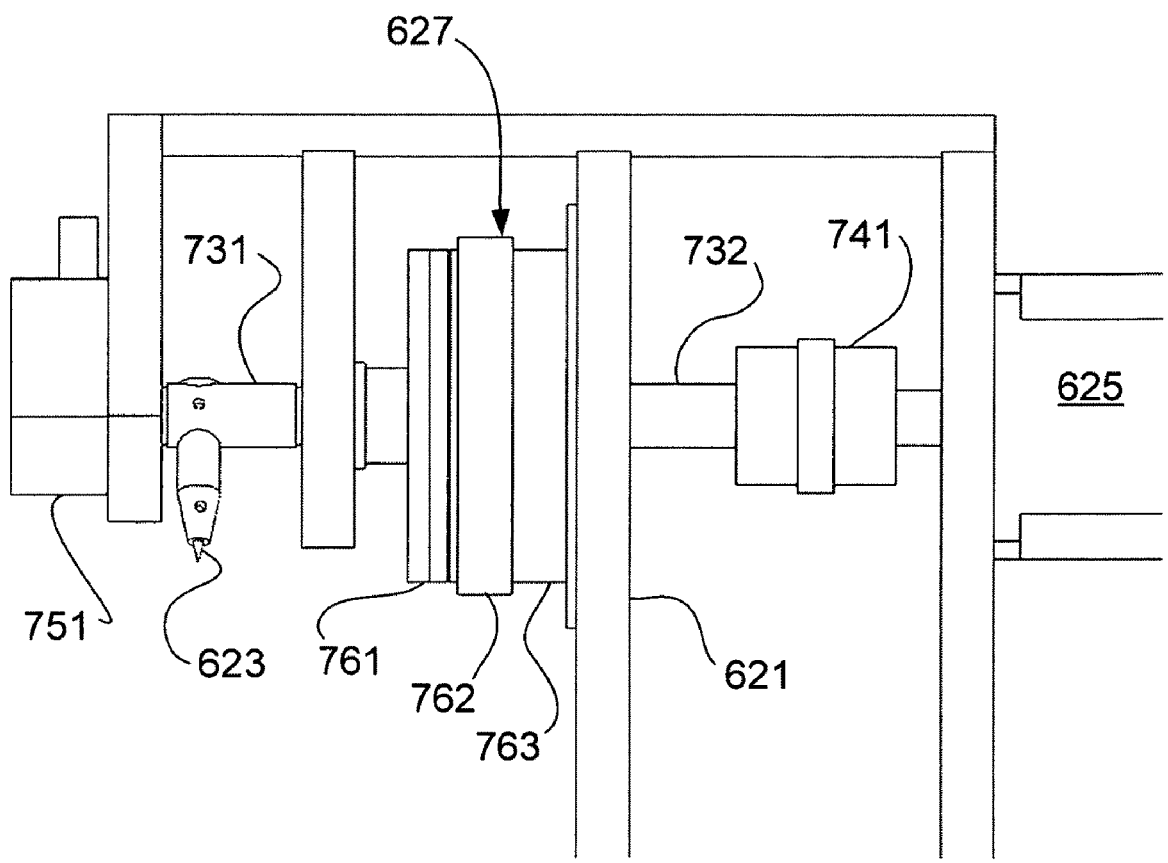
FIG. 7 is a diagram showing the impact system and drive mechanism.

FIG. 7 is a diagram showing the impact system. Depicted are support 621, impact tip 623, motor 625 and clutch 627, as described above in connection with FIG. 6. Also depicted are shafts 731, 732, coupling 741 and shaft encoder 751.

After the alignment, motor 625 is caused to rotate, which drives shaft 732 through its connection with coupling 741. Clutch 627 includes three clutch components 761, 762, 763. Clutch component 761 connects with shaft 731, and clutch component 762 connects with shaft 732. Clutch component 763 provides a magnetic field which causes clutch components 761 and 762 to engage, thereby causing the shaft 731 to quickly reach the speed of shaft 732. Impact tip 623 rotates with shaft 731 and impacts the solder ball (not shown in FIG. 7). Shaft encoder 751 is used to monitor the rotational speed by virtue of its connection with shaft 731.

This configuration is able to provide fast impact speed within a short time period. Clutch 627 may be a magnetic clutch as described or another type of clutch drive system or another type of drive system are given by way of non-limiting examples of techniques to provide a quick ramping of rotational speed and of providing stable impact force through impact tip 623. The use of the clutch provides an ability to quickly achieve rotational speed while maintaining a predetermined momentum of the drive system, and transferring the predetermined momentum to impact tip 623. The motor 625 working through clutch 627 provide sufficient energy to achieve a high linear speed. The high linear speed can be accomplished by motor 625 and clutch 627 using a short rotation arm for impact tip 623.

The impact system is thereby suited for quick acceleration for the purpose of testing of sheer strength. An example of such testing is given in the sheer testing of the solder ball 315 fused to a substrate 317 (FIG. 3), but is also suitable for other types of impact testing. This impact system also can be applied to small scale joint strength measurement.

Sampling System

Figure 8:
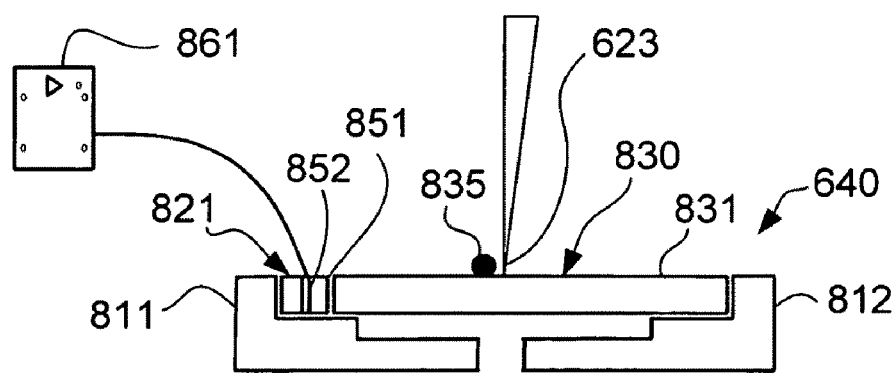
FIG. 8 is a schematic diagram depicting platform and sampling system.

FIG. 8 is a schematic diagram depicting platform and sampling system 640 used in association with tester 600 (FIG. 6). Platform and sampling system 640 includes clamp comprising two clamp halves 811, 812, and piezoelectric sensor 821. Piezoelectric sensor 821 functions as a load cell, which is a type of force transducer, and by way of non-limiting example, is configured as a piezoelectric film sensor. Sensor 821 is positioned between a sample 830 consisting of a substrate 831 and clamp half 811. Substrate 831 has solder ball 835 fused to it. Clamp 811, 812 provides a pre-tightening load to sensor 821. In the example configuration, sensor 821 includes a force distributing layer 851 formed of metal or ceramic which has high hardness. Force distributing layer 851 directly transfers the load to piezoelectric film 852 without absorbing a substantial amount of the force. Electric charge created by the force on piezoelectric film 852 is collected by a charge amplifier 861 for readout according to voltage produced by piezoelectric sensor 821. Piezoelectric sensor 821 advantageously has a high sampling rate; however piezoelectric sensor 821 can be replaced by other force transducers which have the similar characteristics.

The sensing of the force must take into account the pre-tightening force applied by the clamp 811, 812, since the clamping force is not part of the force applied to the solder ball 835. The clamp will apply a pre-tightening force, but it doesn't affect the final results. Consequentially, there is no need to subtract the pre-tightening force from the measured total force results since the piezoelectric material is not sensitive to static loading applied as stable pre-tightening force. Piezoelectric sensor 821 will provide charge only by dynamic loading; however, it needs some calibrations before use.

In the example configuration, piezoelectric sensor 821 is clamped by two force distributing layers, and is responsive to two-sided normal force resulting from pressure on two sides of the piezoelectric film transferred through the two force distributing layers. The electrical signal can thereby be produced by said pressure on the two sides of the piezoelectric film. The pressure applied to sensor 821 is the normal stress, which is vertical to said piezoelectric film sensor. Sensor 821 receives force transferred by copper pieces and metal wire to charge amplifier 861, which is then be collected by an oscillograph or computer to perform analysis. The output from sensor 821 would be linearly proportion to the shear force applied by the impact tip 623. As configured, piezoelectric sensor 821 has force distributing layers on two sides in order to improve the surface contact of sensor 821.

Figure 9:
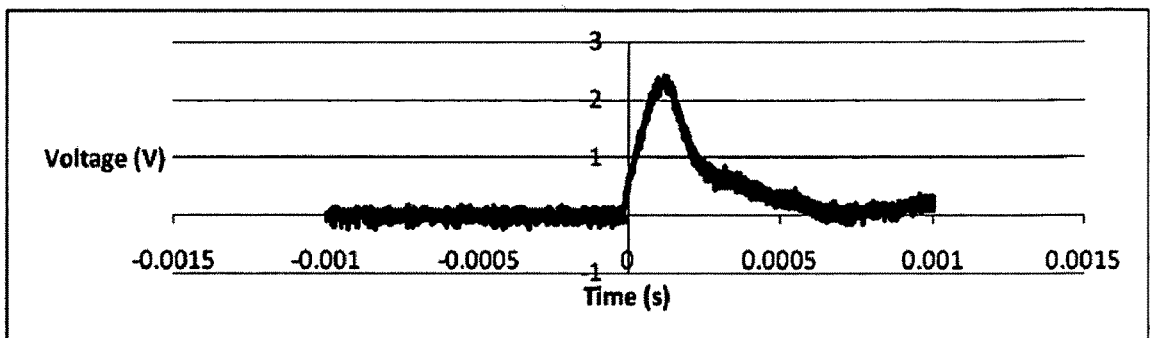
FIG. 9 is a graphical diagram depicting voltage vs. time of a piezoelectric sensor.

FIG. 9 is a graphical diagram depicting voltage vs. time of piezoelectric sensor 821 (FIG. 8). When impact occurs, impact tip 623 provides a high speed load to the solder ball 835, so the solder ball itself or solder joint fixing the solder ball 835 to sample substrate 831 will produce reaction force. Since the clamp 811, 812 is holding substrate 831, substrate 831 will not move, but instead will transfer the force to sensor 821. Therefore, sensor 821's output signal can reflect the real resistance load of sample 830. This sampling system can also be used to measure the high speed or high frequency force or pressure.

While the example configuration shows the force measurement at sampling system 640, it is also possible to measure force at the impact mechanism. Likewise, the rotary movement may be achieved by rotary movement of impact tip 623 or sample 830.

In addition to the force monitoring system, video and other systems for observing the movement of the unit under test are provided, as depicted by camera 630 (FIG. 6).

Experimental Work

Figure 10:
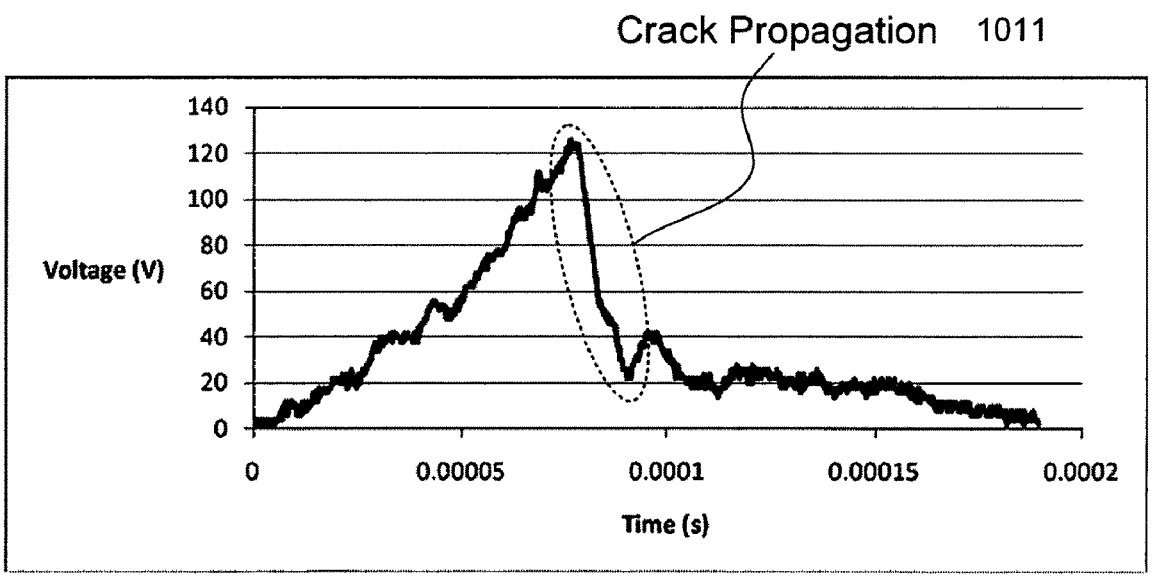
FIG. 10 is a graphical diagram depicting voltage vs. time of a piezoelectric sensor depicting a test performed with a glass test sample.

One wafer level BGA sample was chosen to do the test, which is depicted in FIG. 9, described above. FIG. 10 depicts the test performed with a glass test sample. By using a testing machine similar to that described in connection with FIGS. 6-8, the load versus time curve could be displayed by oscillograph, as depicted in FIG. 9. FIG. 9 shows that the load will vary with the displacement changes. The testing sample was then changed to glass, which is a brittle material, depicted in FIG. 10. From FIG. 10, it can be found that the load quickly falls down after it reaches to peak force, as indicated at 1011. This is because the crack propagates faster than the impact speed, causing a sharp decrease in force. Those two experiments demonstrate the collection of sampling system as reflecting the resistance of an object (e.g., solder ball 835, FIG. 8) to force.

It is possible to obtain the load-time curve by use of sensors and oscillograph at first. It is presumed that the power of motor is much stronger than the solder joint strength; therefore, think the speed is constant during the impact. As a result, it is possible to obtain results by using displacement at a given speed and multiplying by time or by integrating displacement and speed over time.

Six wafer level packages manufactured by four vendors were used in this study for solder joint strength test. Table 1 gives details regarding the packaging technology and the solder balls used per given leg. The alloys of the solder balls were Sn-1Ag-0.5Cu (SAC105) and Sn-1.2Ag-0.5Cu—Ni (LF35).

TABLE 1

Experimental matrix

| Vendor | Leg | WLP Technology | Solder Balls Composition |
|---|---|---|---|
| Vendor 1 | Leg 1 | Double Polyimide Layer | SAC 105 |
| Vendor 2 | Leg 1 | Double Polyimide Layer | SAC 105 |
| Vendor 3 | Leg 1 | Copper Post | SAC 105 |
| Vendor 3 | Leg 2 | Copper Post | LF 35 |
| Vendor 4 | Leg 1 | Double Polyimide Layer | SAC 105 |
| Vendor 4 | Leg 2 | Double Polyimide Layer | LF 35 |

Figure 11:
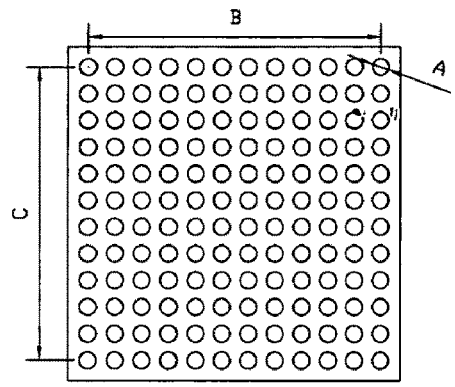
FIGS. 11-13 are diagrams illustrating the package geometry and the detailed information.
Figure 12:
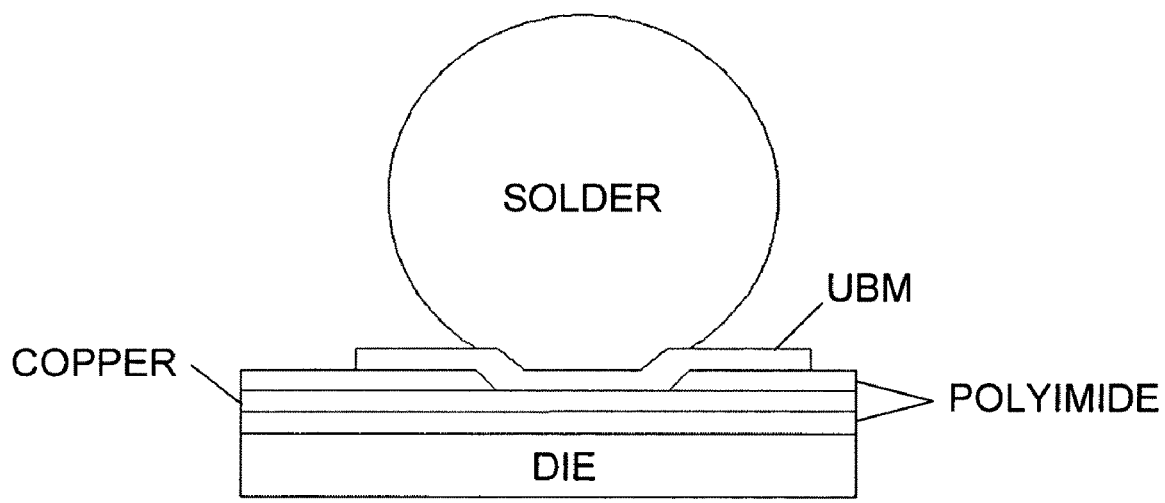
Figure 13:
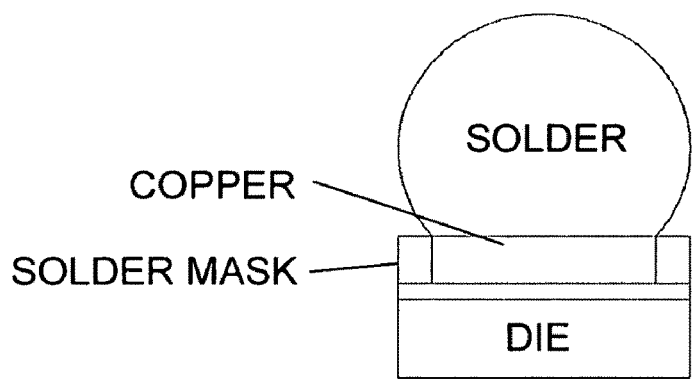
Figure 14A:
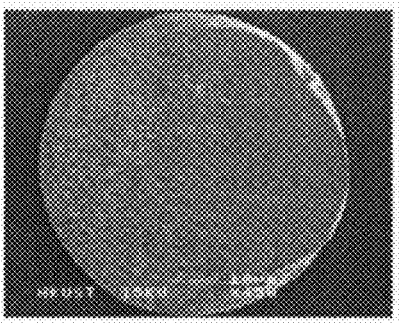
FIGS. 14A-D are SEM micrographs of typical solder ball fracture surfaces tested at different shear speeds.
Figure 14B:
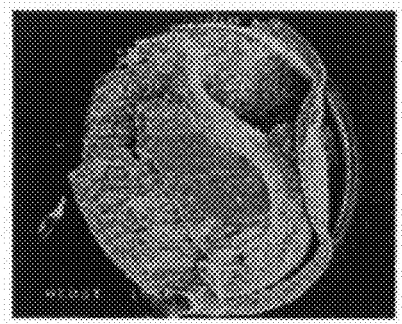
Figure 14C:
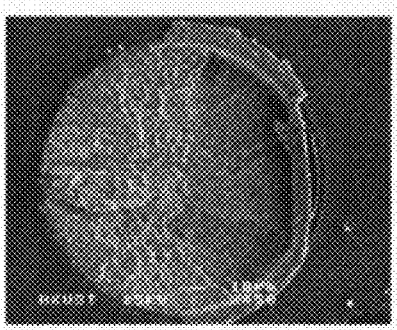
Figure 14D:
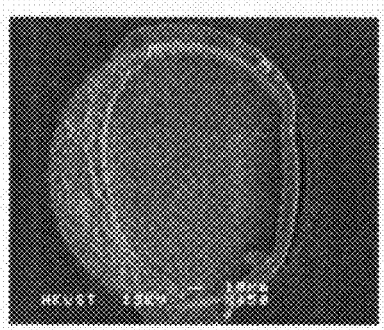

FIGS. 11-13 are diagrams illustrating the package geometry and the detailed information. The parameters are given in Table 2.

TABLE 2

Chip parameters

| Parameter | Distance (μm) |
|---|---|
| A | 250 |
| B | 4400 |
| C | 4400 |

The diameter and height of the balls were 250 μm and 200 μm, respectively. Both static and dynamic shear tests were conducted for those samples. The test conditions are listed in Table 3. Scanning electron microscopy (SEM, JEOL 6300) and EDX (INCA) were applied to investigate the fracture surface after the shear tests.

TABLE 3

Test parameters

| Shear Test Method | Static Shear Test | High Speed Impact Test |
|---|---|---|
| Equipment | DAGE 4000S | Lab-made single ball impact tester |
| Shear Rate | 500 μm/s | 0.5; 1.0; 1.5; 2.0; 2.5; 3.0; 3.5; 4.0 m/s |
| Ram Height | 30 μm | 30 μm |
| Solder Ball Components | SAC105, LF35 | SAC105, LF35 |

Figure 15:
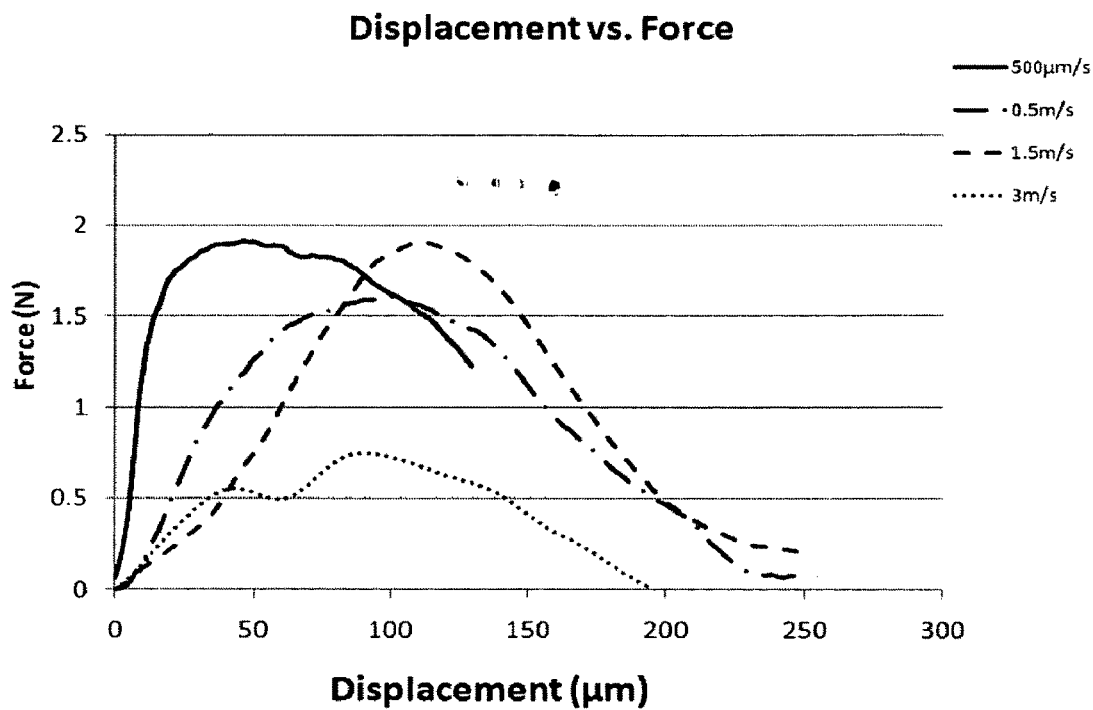
FIG. 15 is a graphical depiction of load-displacement curves.

The sample marked as Vendor 1 Leg 1 was chosen as the typical sample. FIGS. 14A-D are SEM micrographs of typical solder ball fracture surfaces tested at shear speeds ranging from 500 μm/s to 3.0 m/s. It appears that the strain rate had a significant effect on the fracture behavior of the solder joints. With the impact speed increasing, the fracture mode changed from complete ductile (at 500 μm/s and 0.5 m/s) to a semi-ductile (1.5 m/s) and eventually, to brittle fracture (3.0 m/s). The differences in peak stress and elongation at break points are able at different speeds are able to be determined. The corresponding load-displacement curves were recorded and are presented in FIG. 15. It is noted that at a low shear rate of 500 μm/s, the test was stopped after about 130 μm of shearing, because it was tested by another commercial device.

Figure 16:
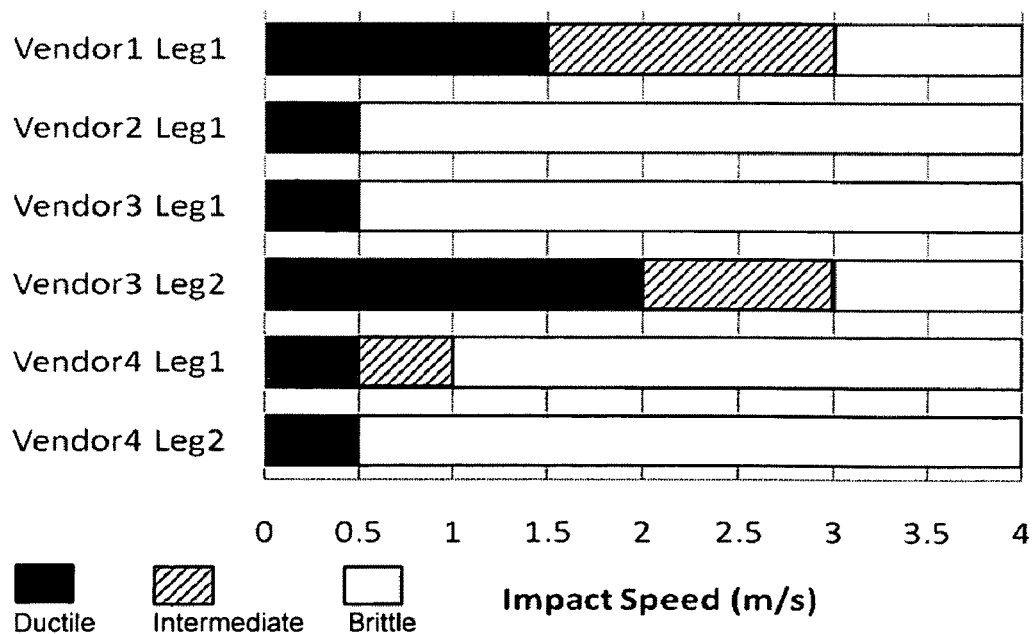
FIG. 16 is a graphical depiction comparing ductile, intermediate and brittle impact responses obtained from the packages from different suppliers.

FIG. 16 is a graphical depiction comparing ductile, intermediate and brittle impact responses obtained from the packages from different suppliers. The depiction compares the fracture mode of the ball joints, i.e. ductile, intermediate (semi-ductile or semi-brittle) or brittle.

By examining the fracture surfaces obtained at various shearing impact speeds, one can establish a way the cracks initiated and propagated. At a low shear rate, when the failure mode was ductile, the fracture cracks started and propagated along the tip movement direction. At a high speed, however, the fracture was interfacial and the cracks followed the intermetallic compound (IMC).

CONCLUSION

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. A test apparatus for applying high speed impact load to a sample to test the shear strength of attachment of a component part to the sample, the test apparatus comprising:
   an impact tip;
   a support mechanism providing an alignment between the impact tip and a portion of the sample to receive a test force, and preventing relative movement of at least one of the sample and the impact tip;
   a rotary drive mechanism including a motor and clutch arrangement capable of applying acceleration to the impact tip in an arc of movement by engagement of the clutch and without restricting the motor to the arc of movement of the impact tip, the rotary drive mechanism capable of establishing an impact force between the impact tip and the sample; and
   a force transducer receiving a force proportional to said impact force and providing a corresponding output.

2. Apparatus according to claim 1, further comprising:
   the motor and clutch arrangement providing sufficient rotary acceleration to apply said high speed impact load by rotation acceleration, while maintaining a momentum established, at least in part, prior to engagement of the clutch.

3. Apparatus according to claim 1 wherein the rotary drive mechanism applies sufficient rotational acceleration to achieve a linear impact speed of at least 0.3 meters per second.

4. Apparatus according to claim 1 wherein the rotary drive mechanism applies sufficient rotational acceleration to achieve a linear impact speed of at least 5 meters per second.

5. The test apparatus of claim 1, further comprising:
   a piezoelectric force transducer positionable in a clamping relationship between the support mechanism and the sample, wherein the piezoelectric transducer provides an electrical signal proportional to the impact force; and
   a clamping mechanism configured to receive, as the sample, a substrate having a solder ball mounted thereon, whereby the piezoelectric force transducer provides information of strength of the solder ball and solder joint strength between the solder ball and the substrate.

6. The test apparatus of claim 1, further comprising:
   a piezoelectric force transducer positionable in a clamping relationship between the support mechanism and the sample, wherein the piezoelectric transducer provides an electrical signal proportional to the impact force; and
   a clamping mechanism receiving the sample on a supporting platform, the clamping mechanism further exerting a preload on the piezoelectric force transducer.

7. Apparatus according to claim 6, wherein the piezoelectric force transducer provides an output linearly proportion to a shear force applied by the impact tip.

8. Apparatus according to claim 6, wherein:
   the piezoelectric force transducer includes two force distributing layers and a piezoelectric sensing layer between the two force distributing layers;
   the piezoelectric force transducer senses two-sided normal force resulting from pressure on two sides of the piezoelectric film transferred through the two force distributing layers; and
   the piezoelectric force transducer provides an output linearly proportion to a shear force applied by the impact tip.

9. Apparatus according to claim 8, further comprising:
   a charge amplifier and a force readout output device to permit analysis.

10. Apparatus according to claim 6, wherein the piezoelectric force transducer includes a piezoelectric film sensor, and a pair of force distributing layer on each of two sides of said piezoelectric film sensor.

11. Apparatus according to claim 1, further comprising:
    a force transducer configured to provide an electrical signal proportional to the impact force, wherein
    the sensor provides an output linearly proportion to a shear force applied by the impact tip.

12. Apparatus according to claim 1, further comprising:
    a piezoelectric force transducer positionable in a clamping relationship between the support mechanism and the sample, wherein the piezoelectric transducer provides an electrical signal proportional to the impact force, wherein
    the piezoelectric force transducer provides an output linearly proportion to a shear force applied by the impact tip,
    wherein, in the case of the clamping establishing a pretightening clamping force, the piezoelectric force transducer provides an initial output corresponding to a pretightening clamping force as a static load applied by the clamp, and
    wherein the piezoelectric force transducer provides a change in its output proportional to the impact force.

13. Apparatus according to claim 12, wherein the piezoelectric force transducer includes a piezoelectric film sensor, and a pair of force distributing layer on each of two sides of said piezoelectric film sensor.

14. Apparatus according to claim 12, wherein said impact tip directly applies force to shear a small testing items.

15. Apparatus according to claim 12, wherein said impact tip directly applies force to shear a solder ball.

16. A method for performing a shear test by applying high speed impact load to a sample to test the shear strength of attachment of a component part to at least a part of the sample, the method comprising:
    providing an impact tip;
    mounting the sample in an impact relationship with the impact tip by using a support mechanism to provide an alignment between the impact tip and a portion of the sample to receive a test force, and preventing relative movement of at least one of the sample and the impact tip;
    applying a rotary movement to one of the impact tip and the sample, thereby establishing an impact force between the impact tip and the sample through the component part; and
    using a force transducer receiving a force between the impact tip and the support mechanism as transferred through the sample, proportional to said impact force and providing a corresponding output to measure the impact force, wherein, in the case of a pre-tightening clamping force applied to the force transducer, the force transducer provides an initial output corresponding to a pre-tightening clamping force as a static load, and wherein the force transducer provides a change in its output proportional to the impact force.

17. The method of claim 16, further comprising:

applying the rotary movement by engaging a clutch to a motor drive, thereby providing sufficient rotary acceleration to apply said high speed impact load by rotation acceleration, while maintaining a momentum established, at least in part, prior to engagement of the clutch.

18. The method of claim 16, further comprising:

receiving, as the sample, a substrate having a solder ball mounted thereon, whereby the force transducer provides information of strength of the solder ball and solder joint strength between the solder ball and the substrate.

19. A method for performing a shear test by applying high speed impact load to a sample to test the shear strength of attachment of a component part to at least a part of the sample, the method comprising:

providing an impact tip;

mounting the sample in an impact relationship with the impact tip by using a support mechanism to provide an alignment between the impact tip and a portion of the sample to receive a test force, and preventing relative movement of at least one of the sample and the impact tip;

applying a rotary movement to one of the impact tip and the sample, thereby establishing an impact force between the impact tip and the sample through the component part; and using a piezoelectric force transducer positionable in a clamping relationship between the support mechanism and the sample, the piezoelectric force transducer receiving a force proportional to said impact force and providing a corresponding output to measure the impact force, wherein, in the case of the clamping establishing a pre-tightening clamping force the piezoelectric transducer provides an initial output corresponding to a pre-tightening clamping force as a static load applied by the clamp, and wherein the piezoelectric force transducer provides a change in its output proportional to the impact force.

20. A test apparatus for applying high speed impact load to a sample to test the shear strength of attachment of a component part to the sample, the test apparatus comprising:

impact contact means;

means for mounting the sample in an impact relationship with the impact tip by using a support mechanism to provide an alignment between the impact tip and a portion of the sample to receive a test force, and preventing relative movement of at least one of the sample and the impact tip;

rotary driver means for applying a rotary movement to one of the impact tip and the sample, by applying short-range acceleration and controllable impact momentum, thereby establishing an impact force between the impact tip and the sample through the component part; and force measuring means for providing a corresponding output to measure the impact force, wherein, in the case of a pre-tightening clamping force applied to the force transducer, the force transducer provides an initial output corresponding to a pre-tightening clamping force as a static load, and wherein the force transducer provides a change in its output proportional to the impact force.

21. Apparatus according to claim 20, wherein the sample includes a substrate having a solder ball mounted thereon and the force measuring means provides information of strength of the solder ball and solder joint strength between the solder ball and the substrate.

* * * * *